United States Patent
Robertson (10) Patent No.: US 11,464,169 B2
(45) Date of Patent: *Oct. 11, 2022

(54) COMBINE HARVESTER CONCAVE THRESHING BAR

(71) Applicant: Brian G. Robertson, Frisco, TX (US)

(72) Inventor: Brian G. Robertson, Frisco, TX (US)

( * ) Notice: Subject to any disclaimer, the term of this patent is extended or adjusted under 35 U.S.C. 154(b) by 25 days.

This patent is subject to a terminal disclaimer.

(21) Appl. No.: 16/826,194

(22) Filed: Mar. 21, 2020

(65) Prior Publication Data

US 2021/0189008 A1 Jun. 24, 2021
US 2021/0380718 A9 Dec. 9, 2021

Related U.S. Application Data

(63) Continuation-in-part of application No. 29/680,208, filed on Feb. 14, 2019, now Pat. No. Des. 954,759,
(Continued)

(51) Int. Cl.
*A01F 12/24* (2006.01)
*A01F 7/04* (2006.01)
(Continued)

(52) U.S. Cl.
CPC ............. *A01F 12/24* (2013.01); *A01F 7/04* (2013.01); *A01F 7/06* (2013.01); *A01F 12/26* (2013.01)

(58) Field of Classification Search
CPC .......... A01F 12/22; A01F 12/24; A01F 12/26; A01F 7/067
See application file for complete search history.

(56) References Cited

U.S. PATENT DOCUMENTS

985 A * 10/1838 Grieb .................... A01D 33/06
460/121
22,141 A * 11/1858 Wells et al. ............ A01F 12/20
460/71
(Continued)

FOREIGN PATENT DOCUMENTS

CA 2297624 A1 1/2001
DE 1111446 B * 7/1961 ............. A01F 12/24
(Continued)

OTHER PUBLICATIONS

PCT/US2018/067237 International Search Report and Written Opinion, dated Mar. 22, 2019, 12 pp. total.
(Continued)

*Primary Examiner* — Thomas B Will
*Assistant Examiner* — Joan D Misa
(74) *Attorney, Agent, or Firm* — Law Office of Sam Sokhansanj PLLC (57) ABSTRACT

A threshing concave assembly is disclosed having a threshing concave bar wherein the threshing bar is comprised of two threshing surfaces having a dihedral angle relationship relative to each other. In addition, in another aspect the threshing bar can be comprised of two dihedral surfaces whereby one surface face has about 130% greater surface area than its adjacent surface face. Alternatively, one surface face of the threshing bar can be 1.3x wider than its adjacent surface face. In another aspect the threshing bar can be comprised of two dihedral surfaces whereby one surface face has about a 170% greater surface area than its adjacent surface face.

13 Claims, 7 Drawing Sheets

Related U.S. Application Data and a continuation-in-part of application No. 29/670,114, filed on Nov. 13, 2018, now Pat. No. Des. 949,930, which is a continuation of application No. 16/159,431, filed on Oct. 12, 2018, now abandoned, and a continuation-in-part of application No. 16/115,331, filed on Aug. 28, 2018, now Pat. No. 10,785,916, said application No. 29/670,114 is a continuation of application No. 16/115,331, filed on Aug. 28, 2018, which is a continuation-in-part of application No. 15/856,381, filed on Dec. 28, 2017, now Pat. No. 10,716,260, and a continuation of application No. 15/856,402, filed on Dec. 28, 2017, now Pat. No. 11,134,613, and a continuation of application No. 15/856,381, filed on Dec. 28, 2017, said application No. 16/115,331 is a continuation-in-part of application No. 15/856,402, filed on Dec. 28, 2017.

(60) Provisional application No. 62/821,570, filed on Mar. 21, 2019.

(51) Int. Cl.
*A01F 7/06* (2006.01)
*A01F 12/26* (2006.01)

(56) References Cited

U.S. PATENT DOCUMENTS

| | | | | |
|---|---|---|---|---|
| 34,617 | A * | 3/1862 | Welsh | A01F 12/26 460/107 |
| 60,778 | A * | 1/1867 | Palmer | A01F 12/20 460/71 |
| 952,795 | A * | 3/1910 | Flynn | A01F 12/24 460/110 |
| 1,573,178 | A * | 2/1926 | McCullough | A01F 12/00 460/120 |
| 1,778,664 | A * | 10/1930 | Dragon | F23H 17/12 126/152 R |
| 2,227,225 | A * | 12/1940 | Lackey | A01F 12/20 460/71 |
| 2,305,964 | A | 12/1942 | Harrison et al. | |
| 2,457,259 | A * | 12/1948 | Fredm | 460/110 |
| 2,457,680 | A | 12/1948 | Johnson | |
| 2,937,647 | A | 5/1960 | Allen et al. | |
| 3,716,060 | A * | 2/1973 | Suzue | A01F 12/24 460/108 |
| 3,891,152 | A * | 6/1975 | Guggenheimer | B02C 13/284 241/88.4 |
| 3,983,883 | A | 10/1976 | Ashton et al. | |
| 4,353,376 | A | 10/1982 | Schuler | |
| 4,875,891 | A | 10/1989 | Turner et al. | |
| 4,889,517 | A * | 12/1989 | Strong | A01F 7/06 460/66 |
| 4,988,326 | A * | 1/1991 | Bennett | A01F 12/24 460/108 |
| 5,024,631 | A * | 6/1991 | Heidjann | A01F 12/26 460/75 |
| 5,569,080 | A * | 10/1996 | Estes | A01F 12/24 460/110 |
| 6,193,604 | B1 | 2/2001 | Ramp et al. | |
| 6,485,364 | B1 * | 11/2002 | Gryspeerdt | A01D 41/1271 460/107 |
| 6,537,148 | B2 | 3/2003 | Schwersmann | |
| 6,958,012 | B2 | 10/2005 | Duquesne et al. | |
| 7,166,026 | B2 * | 1/2007 | Ricketts | A01F 12/26 460/108 |
| 7,207,882 | B2 | 4/2007 | Schmidt et al. | |
| 7,285,043 | B2 | 10/2007 | Foster et al. | |
| 7,749,054 | B2 * | 7/2010 | Farley | A01F 12/22 460/71 |
| 8,313,361 | B2 | 11/2012 | Flickinger et al. | |
| 8,454,416 | B1 * | 6/2013 | Estes | A01F 12/24 460/110 |
| 8,540,559 | B1 * | 9/2013 | Flickinger | A01F 7/067 460/69 |
| 8,636,568 | B1 * | 1/2014 | Farley | A01F 7/067 460/68 |
| 8,690,652 | B1 | 4/2014 | Estes | |
| 8,721,411 | B2 | 5/2014 | Reiger et al. | |
| 9,119,349 | B2 * | 9/2015 | Ricketts | A01F 12/26 |
| 9,215,845 | B2 | 12/2015 | Regier | |
| 9,504,204 | B2 * | 11/2016 | Kile | A01D 41/12 |
| RE46,401 | E | 5/2017 | Estes | |
| 9,723,791 | B1 * | 8/2017 | Kile | A01F 7/06 |
| 9,723,792 | B1 * | 8/2017 | Kile | A01D 41/12 |
| 9,807,939 | B1 * | 11/2017 | Kile | A01F 12/22 |
| 9,913,431 | B2 * | 3/2018 | Van Hullebusch | A01F 12/28 |
| 10,045,487 | B1 * | 8/2018 | Robertson | A01F 12/185 |
| 10,368,492 | B2 * | 8/2019 | Ricketts | A01F 12/20 |
| 10,390,490 | B1 * | 8/2019 | Kile | A01D 41/12 |
| 10,412,895 | B2 * | 9/2019 | Theisen | A01F 12/26 |
| 10,440,893 | B2 * | 10/2019 | Kile | A01F 12/26 |
| 2005/0197176 | A1 | 9/2005 | Foster et al. | |
| 2006/0128451 | A1 | 6/2006 | Ricketts et al. | |
| 2010/0267433 | A1 | 10/2010 | Flickinger et al. | |
| 2011/0143827 | A1 | 6/2011 | Flickinger et al. | |
| 2011/0151951 | A1 | 6/2011 | Regier et al. | |
| 2014/0087793 | A1 * | 3/2014 | Regier | A01F 12/22 460/59 |
| 2015/0250101 | A1 | 9/2015 | Kile | |
| 2016/0295802 | A1 * | 10/2016 | De Witte | A01F 12/22 |
| 2016/0353662 | A1 | 12/2016 | Haus et al. | |
| 2017/0347529 | A1 | 12/2017 | Bussman et al. | |
| 2018/0359926 | A1 * | 12/2018 | Estes | A01F 11/06 |
| 2018/0368325 | A1 | 12/2018 | Koudela | |
| 2019/0166767 | A1 * | 6/2019 | Robertson | A01F 12/184 |
| 2019/0166768 | A1 * | 6/2019 | Robertson | A01F 12/184 |

FOREIGN PATENT DOCUMENTS

| | | | | |
|---|---|---|---|---|
| FR | 1370285 | A * | 8/1964 | A01F 12/24 |
| KR | 20040012630 | A | 2/2004 | |
| WO | WO0124609 | A1 | 4/2001 | |
| WO | WO-2018237234 | A1 * | 12/2018 | A01F 12/26 |

OTHER PUBLICATIONS

PCT/US2018/067245 International Search Report and Written Opinion, dated Mar. 25, 2019, 44 pp. total.
PCT/US2018/067256 International Search Report and Written Opinion, dated Mar. 22, 2019, 39 pp. total.
PCT/US2018/067262 International Search Report and Written Opinion, dated Apr. 2, 2019.
Peter Miu, "Combine Harvesters Theory, Modeling, and Design," 2016, CRC Press, 485 pp. total.

* cited by examiner

FIG. 6A ic # COMBINE HARVESTER CONCAVE THRESHING BAR

CROSS-REFERENCE TO RELATED APPLICATIONS

This application claims the benefit of U.S. Provisional Application No. 62/821,570 filed on Mar. 21, 2019, which is incorporated herein by reference. This application is also a continuation-in-part (CIP) of U.S. Non-Provisional application Ser. No. 16/115,331 filed on Aug. 28, 2018, which is incorporated herein by reference in its entirety, which is a CIP of U.S. Non-Provisional application Ser. No. 15/856,381 filed on Dec. 28, 2017, which is incorporated herein by reference in its entirety, and a CIP of U.S. Non-Provisional application Ser. No. 15/856,402, filed on Dec. 28, 2017, which is incorporated herein by reference in its entirety. This application is also a CIP of U.S. Design Pat. application No. 29680208 filed on Feb. 14, 2019, which is incorporated herein by reference in its entirety. This application is also a CIP of U.S. Design Pat. application No. 29670114 filed on Nov. 13, 2018, which is incorporated herein by reference in its entirety, which is a continuation of U.S. Non Provisional Application Ser. No. 16/159,431 filed on Oct. 12, 2018, which is a continuation of U.S. Non-Provisional application Ser. No. 16/115,331 filed on Aug. 28, 2018, which is a continuation of U.S. Non-Provisional application Ser. No. 15/856,381 filed on Dec. 28, 2017, which is a continuation of U.S. Non Provisional application Ser. No. 15/856,402, filed on Dec. 28, 2017.

BACKGROUND

This section is intended to introduce the reader to aspects of art that may be related to various aspects of the present disclosure described herein, which are described and/or claimed below. This discussion is believed to be helpful in providing the reader with background information to facilitate a better understanding of the various aspects of the present disclosure described herein. Accordingly, it should be understood that these statements are to be read in this light, and not as admissions of prior art.

A combine harvester is a machine that is used to harvest grain and seed crops. The objective is to complete several processes, which traditionally were distinct, in one pass of the machine over a particular part of the field. Among the crops that may be harvested with a combine can include but is not limited to wheat, oats, rye, peas, edible beans, barley, corn, soybeans, and flax or linseed. The waste (e.g., straw) left behind on the field includes the remaining stems and leaves of the crop having limited nutrients which may be, for example, chopped and spread on the field or baled for feed and bedding for livestock. Generally, the combine harvester includes a header, which removes the crop from a field, and a feeder housing which transports the crop matter into a threshing rotor. The process of threshing is removing the grain or seed from the crop. The threshing rotor can include one or more rotors which can extend axially (front to rear) or transversely within the body of the combine, and which are partially or fully surrounded by one or more perforated concaves. In particular, there may be a rotor having threshing concaves with bars or wires for threshing operations of the crop, and concave grates with slots, wires or fingers for separation operations of the crop material, also known as separation concaves or separation grates. Generally, the separation grate is meant to separate any grain that is caught in material other than grain, such as chaff, straw, shucks, stalk, leafy material, among others, which may also be referred to herein as MOG.

However, current conventional concave bars and separation grates have certain configurations that are not optimized to minimize grain damage while simultaneously maximizing threshing and separating of the crop material, thereby resulting in inefficient harvesting, damaged, and wasted crop. In one example of traditional combine concaves, if a combine harvester has three concaves, then a crop that is threshed in a first concave, has a two-third probability for the threshed grains to fall through the concave openings. However, if the crop does not get threshed until the second concave, then it only has a one-third probability for the threshed grains to fall through the concave openings. Further, if the crop is not threshed in the second concave, then the third concave can become overloaded with crop and grain material and operating at over capacity, thus resulting in the grain being discharged out the back of the combine and resulting in very inefficient harvesting.

What is needed is a concave bar configuration that optimizes the surface area of the dihedral faces of concave threshing bars that have certain threshing angles and surface areas that minimizes grain damage while maximizing threshing effectiveness.

BRIEF SUMMARY

In one aspect of the disclosure described herein, a concave bar configuration provides a balance of being as aggressive as possible while doing the least amount of grain damage. The concave bar configuration of the disclosure described herein can thresh crop effectively such it has the most chance to be captured in a combine, while also threshing the crop with the least amount of grain damage, such that the seed or grain is without cracks or splits.

In another aspect of the disclosure described herein, a threshing concave assembly is disclosed having a threshing concave bar wherein the threshing bar is comprised of two threshing surfaces having a dihedral angle relationship relative to each other. In addition, in another aspect the threshing bar can be comprised of two dihedral surfaces whereby one surface (face) has about 130% greater surface area than its adjacent surface. Alternatively, one face of the threshing bar can be 1.3x longer/wider than its adjacent face. In addition, the threshing bar can be comprised of two dihedral surfaces whereby one surface has about 150% greater surface area than its adjacent face. Further, in another aspect the threshing bar can be comprised of two dihedral surfaces whereby one surface has about a 170% greater surface area than its adjacent face. In addition, in another aspect the threshing bar is comprised of two dihedral surfaces whereby one surface is about 100% to 250% greater surface area than the adjacent face. Also, the threshing bars in the concave can be of varying face surface areas relative to each other, such as wherein threshing bars' surfaces/faces are equal, some bars have a surface that is 130% greater than its adjacent face and some bars have a surface that is say 170% greater than its adjacent face, among others.

In another aspect of the disclosure described herein, a concave threshing bar is disclosed having a first and second threshing opposing faces, wherein the first face comprises a surface area larger than the second face. In addition, the surface area of the first face is about 130% larger or wider or about 1.3 times larger or wider than the second face. In addition, the surface area of the first face is about 170% larger or wider or about 1.7 times larger or wider than the second face. Further, the surface area of the first face is about 101% to 199% larger or wider or about 1.01 times up to 1.99 times larger or wider than the second face. In another aspect of the disclosure described herein, a concave threshing bar is disclosed having a plurality of threshing bars, wherein the threshing bars are of varying face surface areas relative to each other. In addition, the threshing bars are of varying dihedral angles.

In addition, in another aspect the threshing bars in the concave can be of varying dihedral angles, such as threshing bars of various threshing angles throughout the concave, with more aggressive bars having a 45-degree angle near where crop enters the concave and then having bars that are anywhere from about 25 to 45 degrees or less aggressive as crop is threshed. In addition, in another aspect the threshing bars in the concave can be of various spacing between adjacent bars, wherein some bars in the concave are spaced closer or farther apart than other bars whereby the majority of grain is threshed, more grain can escape. Here, the faster the grain can escape, the less grain damage there is. Further, in another aspect the threshing bars in the concave can be of various dihedral angles and spacing between adjacent bars, such as bars that are not only of different angle but also of different spacing. In addition, in another aspect the threshing bar can be comprised of two dihedral surfaces wherein the bars are fastened or secured to one or more side rails of the concave at an acute angle. Here, this can include wherein the bars are diagonal in the concave, such that the crop can hit the bar more "head on."

In another aspect the threshing bar can be comprised of dihedral faces that are laser hardened. In this method, the threshing bar metal can be hardened by a laser such that it maintains the bar angle and extends the bars life, otherwise the threshing surface (face of the bar) can get worn down and becomes less effective. In another aspect the threshing bar can be comprised of dihedral faces that is case hardened. In this method of hardening steel, however, the laser hardening is more precise and cost effective. With case hardening, one can harden the entire bar relative to a laser where one can harden a specific area. In another aspect, wherein the sharp edges of the threshing bar can be made less sharp (rounded off) and laser hardened. Here, this would provide for maximum bar life by just barely rounding off the sharp threshing edge, which are usually the first to get worn down, then case hardening that edge giving it maximum efficiency. Accordingly, by taking the small edge down exposes more surface area that can be hardened, which would become exposed more quickly. In another aspect, the threshing bar can be extruded.

The above summary is not intended to describe each and every disclosed embodiment or every implementation of the disclosure. The Description that follows more particularly exemplifies the various illustrative embodiments.

BRIEF DESCRIPTION OF THE DRAWINGS

The following description should be read with reference to the drawings, in which like elements in different drawings are numbered in like fashion. The drawings, which are not necessarily to scale, depict selected embodiments and are not intended to limit the scope of the disclosure. The disclosure may be more completely understood in consideration of the following detailed description of various embodiments in connection with the accompanying drawings, in which.

DETAILED DESCRIPTION

In the Brief Summary of the present disclosure above and in the Detailed Description of the disclosure described herein, and the claims below, and in the accompanying drawings, reference is made to particular features (including method steps) of the disclosure described herein. It is to be understood that the disclosure of the disclosure described herein in this specification includes all possible combinations of such particular features. For example, where a particular feature is disclosed in the context of a particular aspect or embodiment of the disclosure described herein, or a particular claim, that feature can also be used, to the extent possible, in combination with and/or in the context of other particular aspects and embodiments of the disclosure described herein, and in the disclosure described herein generally.

The embodiments set forth below represent the necessary information to enable those skilled in the art to practice the disclosure described herein and illustrate the best mode of practicing the disclosure described herein. In addition, the disclosure described herein does not require that all the advantageous features and all the advantages need to be incorporated into every embodiment of the disclosure described herein.

Here, it has been observed that that maximizing surface area of the concave threshing bar is critical to maximizing threshing effectiveness. More specifically, it has been observed in the disclosure described herein that more threshing surface area on the bottom face or the threshing face of the concave bar can have a profound impact on grain harvesting, efficiency, and the quality of the grain. In other words, if there are two threshing concave bars of same threshing surface areas, but with one having a different concave face length, the one with an alternative concave face length may be preferred with respect to threshing efficiency and grain damage/quality.

In particular, what has been established here in the disclosure described herein according to the one or more embodiments is that along with concave bar threshing surface area (top face or bottom face) is a very important factor for consideration the concave bar design. In particular, it has been observed that maximum threshing efficiency and grain quality is not achieved by just maximizing the surface area but is also the location of where that surface area is on the concave bar.

In particular, when an about 45-degree bar (FIG. 1D) with a threshing face of about 1.0x size of the bottom threshing face is compared to another about 45-degree or 45-degree bar with a threshing face 1.7x (170%) the bottom face (FIG. 6A), it was observed that there are significant differences in performance (mainly grain damage) despite their surface areas across the entire bars are the same. Accordingly, it has been observed that the same kernel of corn can be removed with an about 25-degree bar with threshing face 1.7x (170%) wider times the bottom face as with a 45-degree bar with threshing face 1.0x the bottom face (each of the bars having the same diameters), whereas the about 25-degree bar does significantly less grain damage.

Accordingly, what has been observed through testing, the larger the angle of the concave bar, the greater the force that is applied onto the crop and causing grain damage. Hence, by using what we just established, one can decrease the force (lesser the angle) but at the same time lengthen or widen one or more of the threshing faces or increase one or more of the threshing face surface areas, so less force is applied but for slightly longer, thus resulting less grain damage.

Figure 1A:
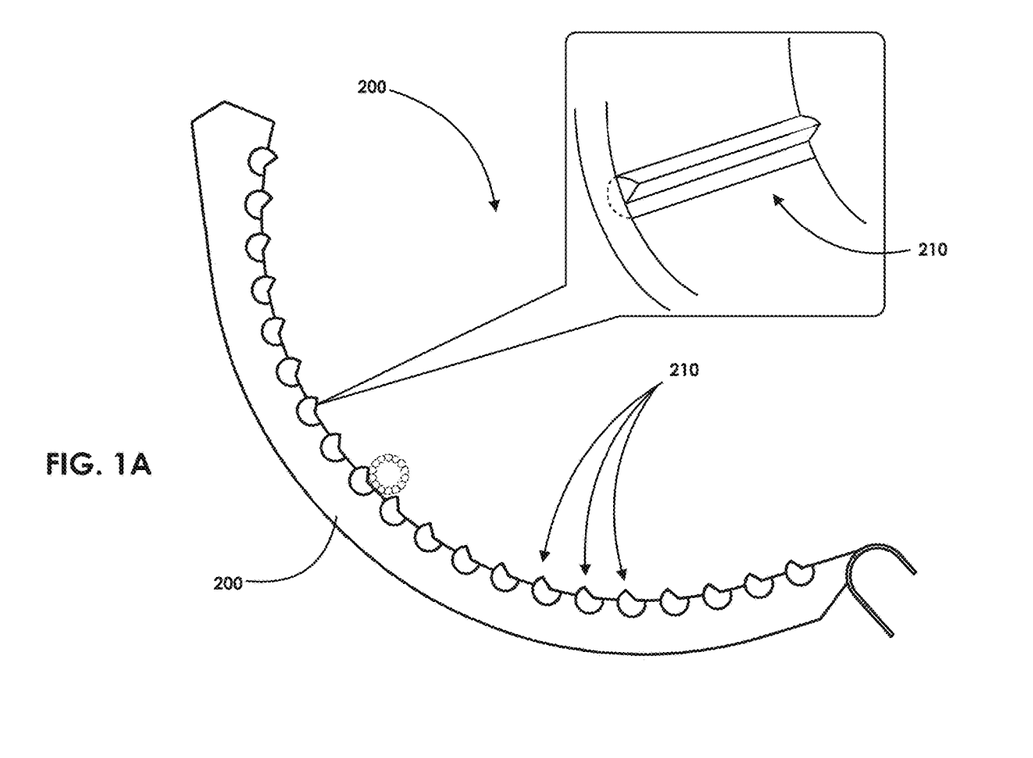
FIG. 1A illustrates a simplified cross-sectional side view and a close-up perspective view for one non-limiting exemplary embodiment of one or more bars or rods of the concave bar and frame assembly of the disclosure described herein.
Figure 1B:
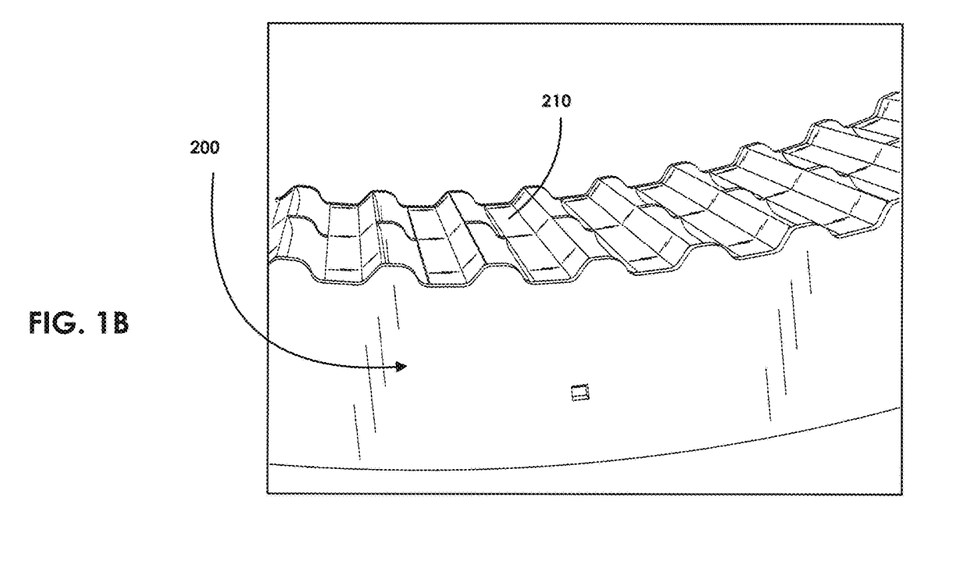
FIG. 1B illustrates a perspective side view for the concave bar and frame assembly of FIG. 1A.
Figure 1C:
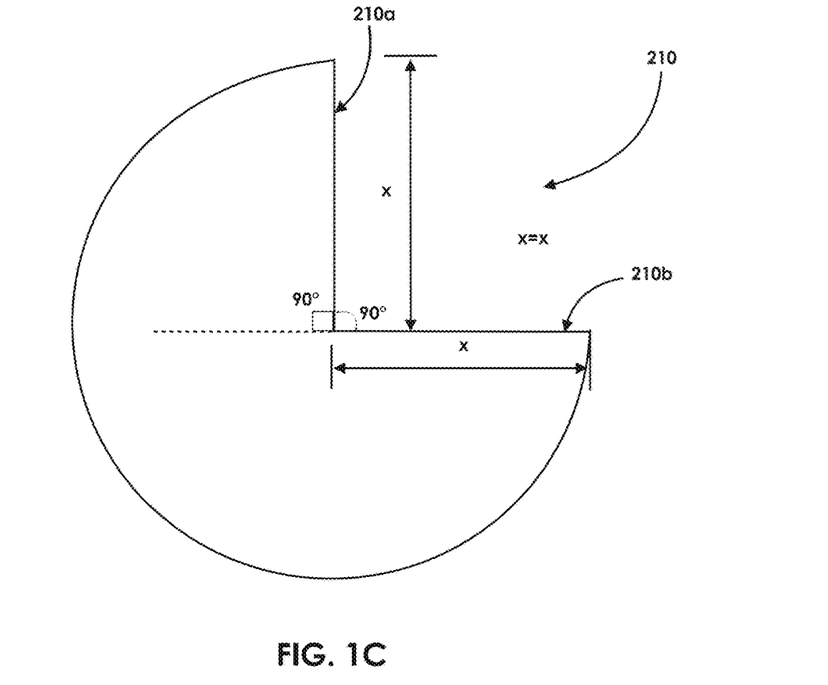
FIG. 1C illustrates a cross-sectional side view of a concave bar according to one non-limiting exemplary embodiment of the disclosure described herein.
Figure 1D:
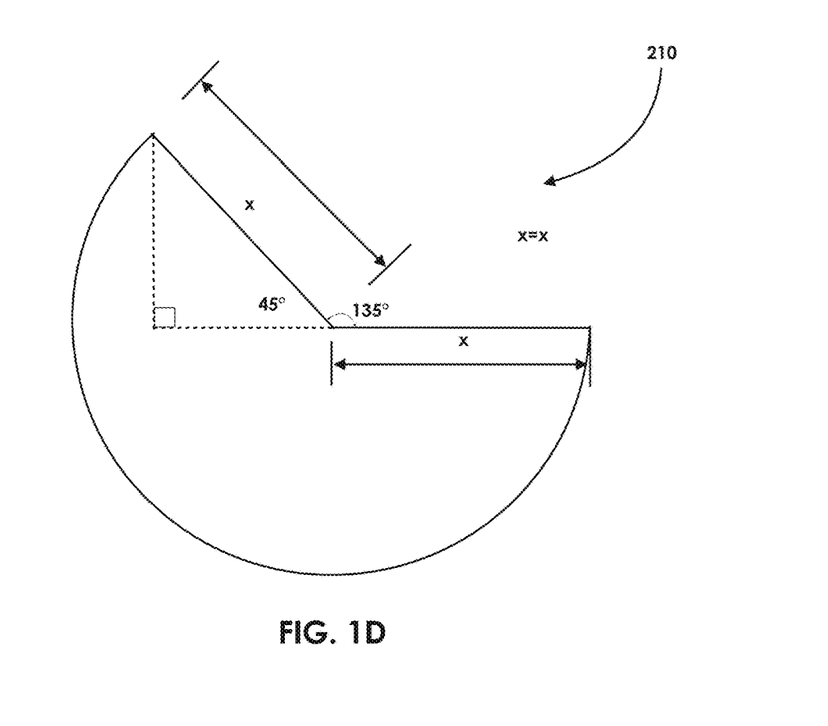
FIG. 1D illustrates a cross-sectional side view of a concave bar according to another non-limiting exemplary embodiment of the disclosure described herein.
Figure 2A:
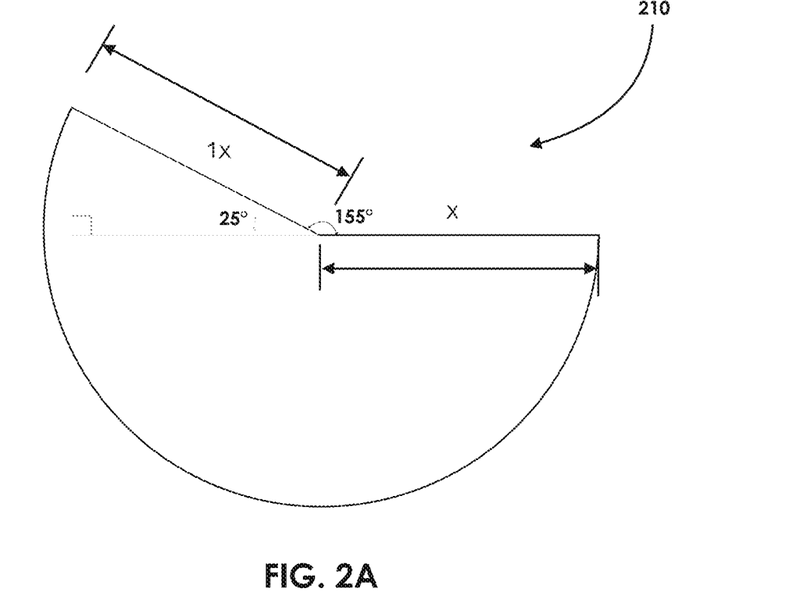
FIG. 2A illustrates a cross-sectional side view of a concave bar according to another non-limiting exemplary embodiment of the disclosure described herein.
Figure 2B:
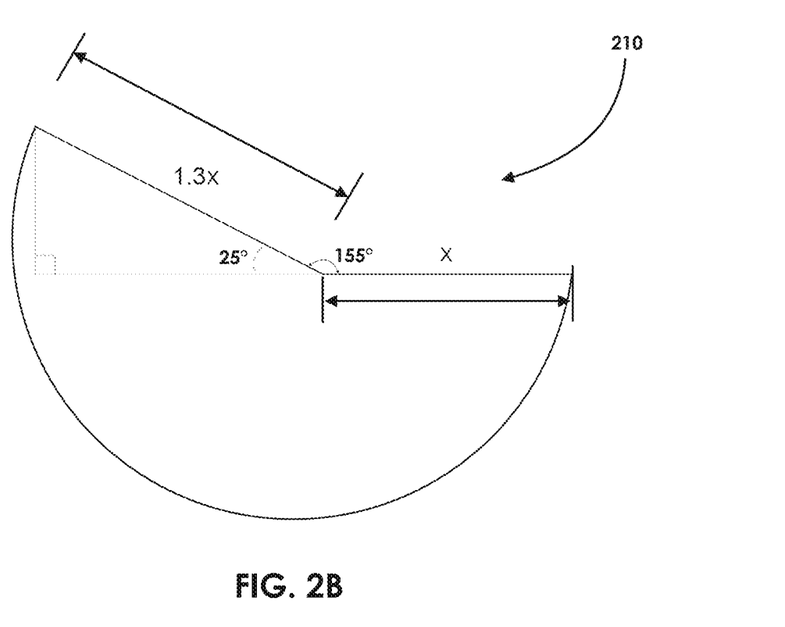
FIG. 2B illustrates a cross-sectional side view of a concave bar according to another non-limiting exemplary embodiment of the disclosure described herein.
Figure 3A:
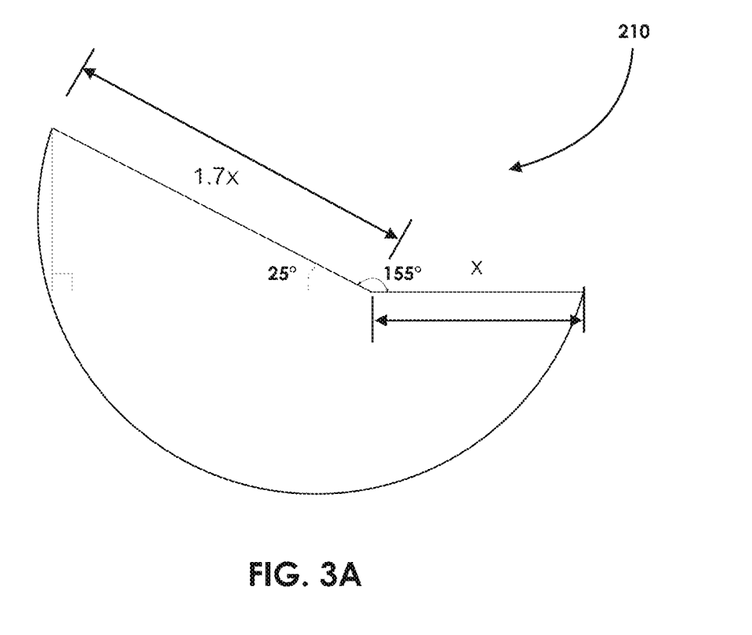
FIG. 3A illustrates a cross-sectional side view of a concave bar according to another non-limiting exemplary embodiment of the disclosure described herein.

FIGS. 1A-1B illustrate a concave frame assembly 200 and concave bars 210 for one or more non-limiting exemplary embodiments of the disclosure described herein. As disclosed herein, references to top or bottom faces of the threshing bars 210 may also be interpreted as first or second faces of the threshing bars. FIG. 1C illustrates an about 90-degree concave bar having equal first face (210*a*) and second face (210*b*) surface areas or heights/widths (x). FIG. 1D illustrates an about 45-degree concave bar (or about 135-degree) having substantially equal top and bottom surface areas or heights/widths (x). FIG. 2A illustrates a concave bar having an about 25-degree angle (or about 155-degree) and both the top and bottom surfaces each having substantially equal surface areas or height/widths (x). FIG. 2B illustrates a concave bar having an about 25-degree angle (or about 155-degree) and having a top face surface area or height/width that is about 1.3x (130%) larger than the bottom face surface area or height/width (x). FIG. 3A illustrates a concave bar having an about 25-degree angle (or about 155-degree) with a top face surface area or height/width that is about 1.7x (170%) larger than the bottom face surface area or height/width (x).

Figure 3B:
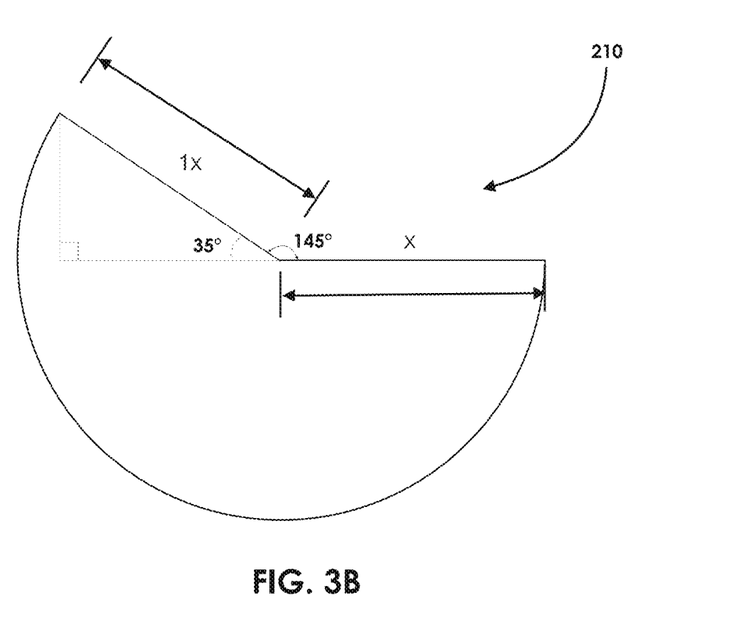
FIG. 3B illustrates a cross-sectional side view of a concave bar according to another non-limiting exemplary embodiment of the disclosure described herein.
Figure 4A:
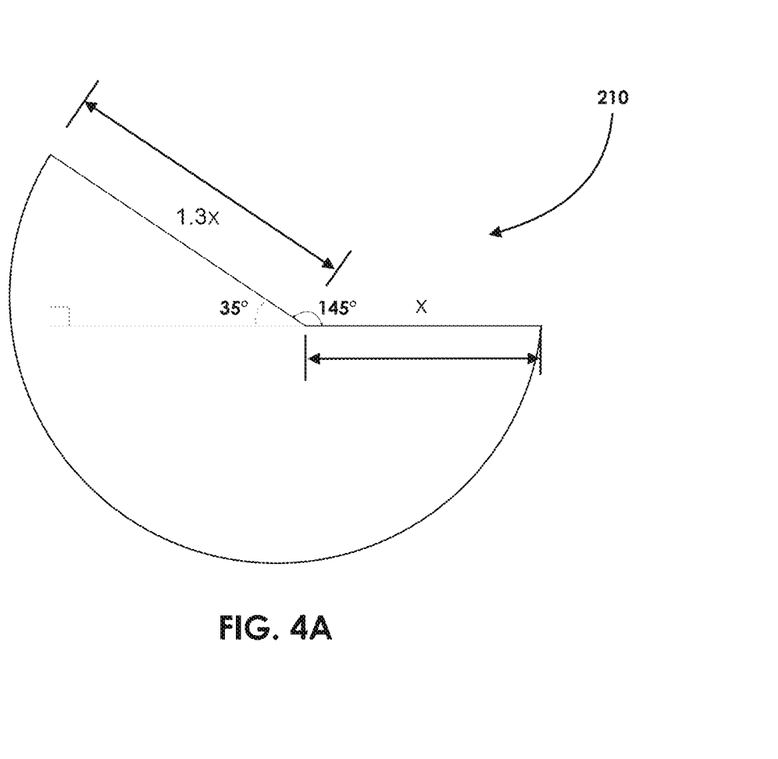
FIG. 4A illustrates a cross-sectional side view of a concave bar according to another non-limiting exemplary embodiment of the disclosure described herein.
Figure 4B:
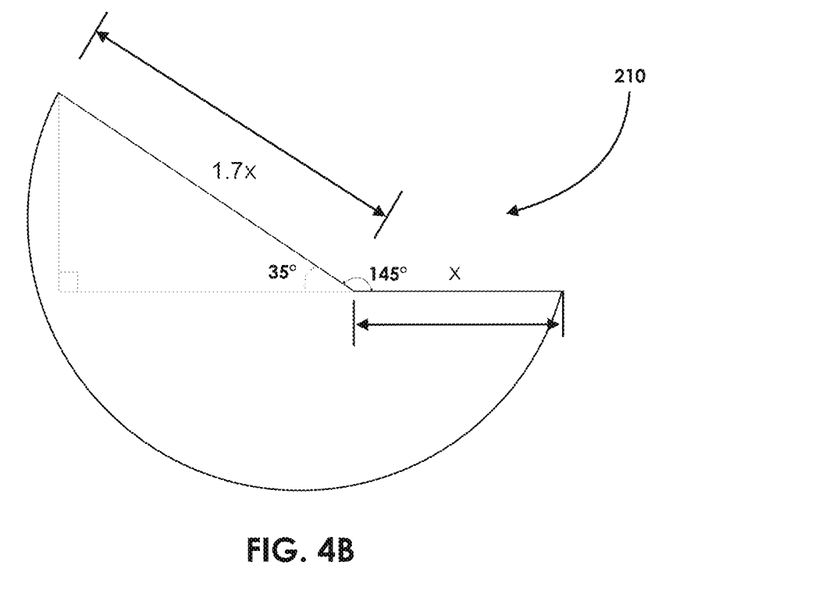
FIG. 4B illustrates a cross-sectional side view of a concave bar according to another non-limiting exemplary embodiment of the disclosure described herein.
Figure 5A:
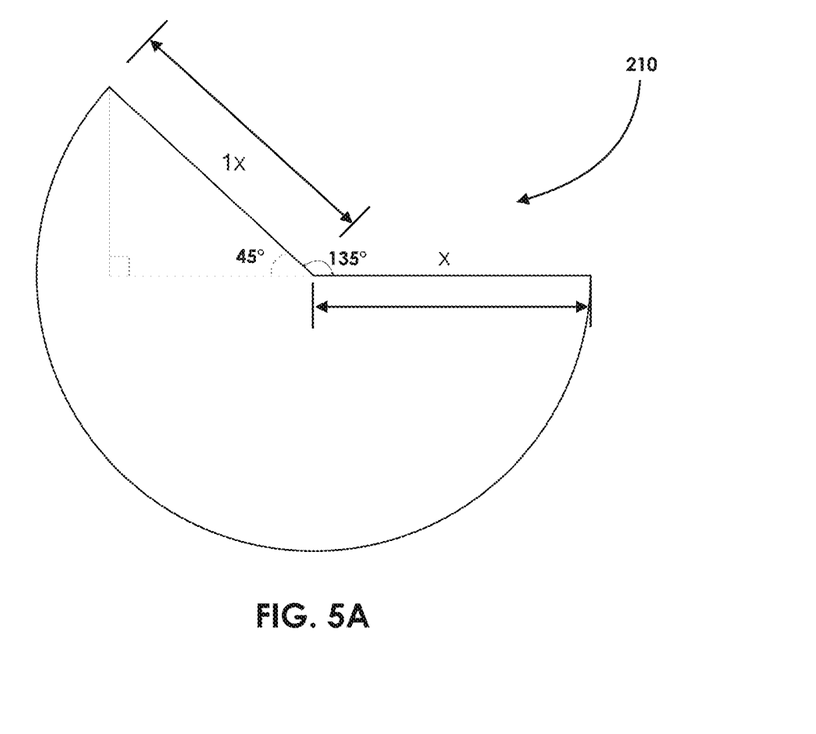
FIG. 5A illustrates a cross-sectional side view of a concave bar according to another non-limiting exemplary embodiment of the disclosure described herein.
Figure 5B:
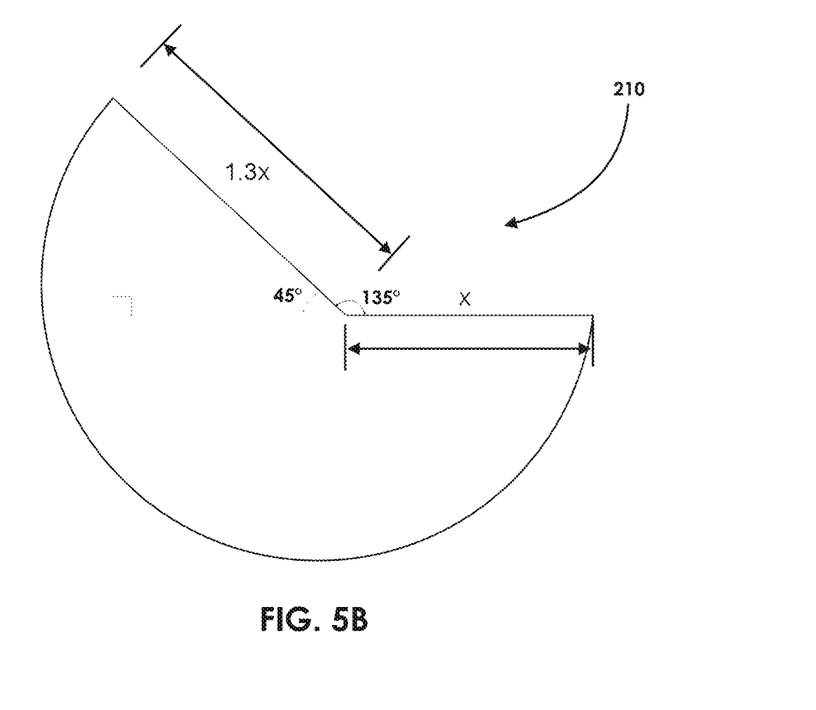
FIG. 5B illustrates a cross-sectional side view of a concave bar according to another non-limiting exemplary embodiment of the disclosure described herein.
Figure 6A:
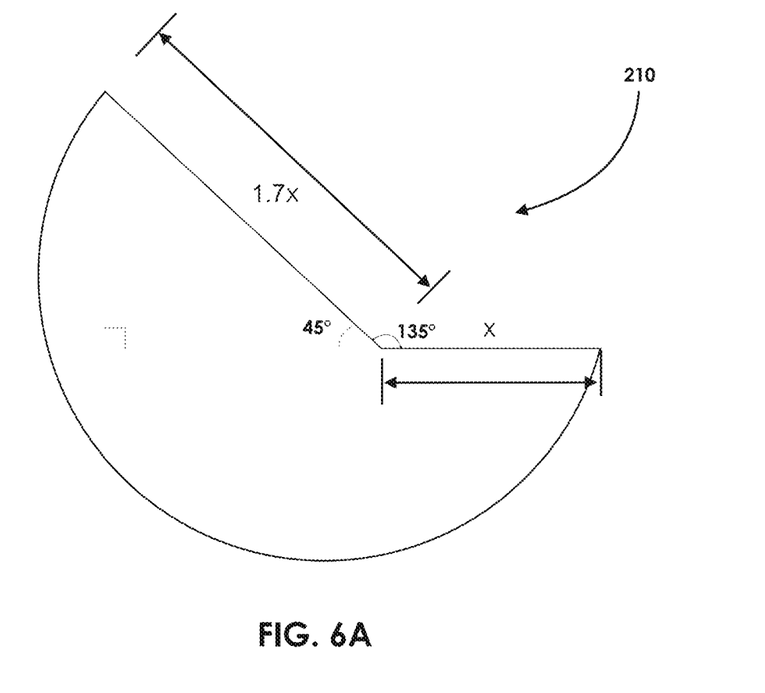
FIG. 6A illustrates a cross-sectional side view of a concave bar according to another non-limiting exemplary embodiment of the disclosure described herein.

FIG. 3B illustrates a concave bar having an about 35-degree angle (or about 145-degree) with a top surface area height/width (x) that is equal to its bottom surface area or height/width (x). FIG. 4A illustrates a concave bar having an about 35-degree angle (or about 145-degree) with a top face surface area or height/width that is about 1.3x (130%) larger than its bottom face surface area or height/width (x). FIG. 4B illustrates a concave bar having an about 35-degree angle (or about 145-degree) with a top surface area or height/width that is about 1.7x (170%) larger than its bottom face surface area or height/width (x). FIG. 5A illustrates a concave bar having an about 45-degree angle (or about 135-degree) with a top face surface area or height/width (x) that is equal to the bottom surface area or height/width (x). FIG. 4B illustrates a concave bar having an about 45-degree angle (or about 135-degree) with a top face surface area or height/width that is about 1.3x (130%) larger than the bottom face surface area or height/width (x). FIG. 6A illustrates a concave bar having an about 45-degree angle with a top face surface area or height/width that is about 1.7x (170%) larger than the bottom surface area or height/width (x).

With respect to the concave bar angles disclosed in FIGS. 2A-6A, such as 25-degrees, 35-degrees, and 45-degrees, it is contemplated within the scope of the disclosure described herein that that any of the aforementioned angles may also be from about 10-degrees up to and including 90-degrees, with either the top or bottom threshing bar face surface areas or width/heights having ratios relative to each ranging from 1:2, 2:1, or 3:1, among others.

TABLE 1 illustrates test data for an exemplary crop, here a corn cob with a 2-inch cob surface, used in combination with an about 90-degree concave threshing bars in a combine harvester concave having substantially equal top and bottom threshing surfaces areas or height/width, as shown with respect to FIG. 1C:

TABLE 1

| THRESHING ANGLE | THRESHING FACE MULTIPLE | THRESHING EFFICIENCY | % DAMAGE |
|---|---|---|---|
| Ideal |  | 100.00% | 0.00% |
| 90° | 1.0x | 88.0% | 10.2% |

TABLE 2 illustrates the various test data for the exemplary tested crop, here a corn cob with a 2-inch cob surface, and the concave threshing bars within the concave each having top and bottom surfaces of substantially the same surface areas or height/width (e.g., 1.0x, x=x, or 1:1) and the various bar configurations and surface areas or height/widths of one surface relative to another (about 1.0x, 1.3x, or 1.7x) corresponding to each of FIGS. 1D-6A of the disclosure described herein:

TABLE 2

| THRESHING ANGLE | THRESHING FACE MULTIPLE | THRESHING EFFICIENCY | % DAMAGE |
|---|---|---|---|
| Ideal |  | 100.00% | 0.00% |
| 45° or 135° | 1.0x | 98.0% | 6.0% |
| 35° or 145° | 1.0x | 97.0% | 5.0% |
| 25° or 155° | 1.0x | 94.3% | 4.0% |
| 45° or 135° | 1.3x | 98.3% | 9.0% |
| 35° or 145° | 1.3x | 97.5% | 3.0% |
| 25° or 155° | 1.3x | 96.4% | 2.0% |
| 45° or 135° | 1.7x | 98.8% | 10.0% |
| 35° or 135° | 1.7x | 99.3% | 2.0% |
| 25° or 155° | 1.7x | 98.7% | 1.0% |

Referring to TABLES 1-2, as shown from the testing results, the about 25-degree angled threshing bar (or about 155-degree) having an about 1.7x top surface relative to the bottom surface, as shown in FIG. 3A, demonstrated the least amount of damage to the crop at a rate of 1.0% while still maintaining a high threshing efficiency at a rate of 98.7% that exceeded the 45-degree bar (1.0x). Accordingly, the foregoing results demonstrate that the embodiment of FIG. 3A will provide the least amount of damage to a crop in a combine harvester concave while maintaining high crop threshing efficiency. Similarly, the about 35-degree angled threshing bar (or about 145-degree) having an about 1.7x top surface relative to the bottom surface, as shown in FIG. 4A, demonstrated the highest threshing efficiency rate of 99.3% while still maintaining a low crop damage rate of 2.0%. Hence, the foregoing results demonstrate that the embodiment for FIG. 4A will provide the highest crop threshing efficiency rate in a combine harvester concave while maintaining a low damage rate to the crop. Moreover, the about 90-degree threshing concave bar with substantially equal first and second face surface areas of FIG. 1C demonstrated to be the least efficient (88.0%) concave bar and with the most damage to the crop (10.2%).

Here, it is contemplated within the scope of the disclosure described herein that any of the concave threshing bar 210 embodiments of FIGS. 1C-6A can be used within the concave frame assembly 200 of FIGS. 1A-1B, in any configuration, including forward facing or reverse facing arrangements of bars 210 within the concave. In addition, it is contemplated within the scope of the disclosure described herein that any threshing bars disclosed in FIGS. 1A-1B can be used in combination with each other within the concave frame 200, such as in varying spacing relative to each other or in diagonal/sideways configurations.

From the foregoing it will be seen that the present disclosure described herein is one well adapted to attain all ends and objectives herein-above set forth, together with the other advantages which are obvious and which are inherent to the invention.

Since many possible embodiments may be made of the invention without departing from the scope thereof, it is to be understood that all matters herein set forth or shown in the accompanying drawings are to be interpreted as illustrative, and not in a limiting sense.

While specific embodiments have been shown and discussed, various modifications may of course be made, and the invention is not limited to the specific forms or arrangement of parts described herein, except insofar as such limitations are included in following claims. Further, it will be understood that certain features and sub-combinations are of utility and may be employed without reference to other features and sub-combinations. This is contemplated by and is within the scope of the claims.

What is claimed is:

1. A concave threshing bar, comprising:
    a cylindrical threshing bar comprising a channel extending a length of the threshing bar, wherein the threshing bar is secured to a concave; and
    the channel of the threshing bar comprising a first face and a second face, wherein the second face is axially aligned with a horizontal plane and the first face is at an angle greater than 90° relative to the second face, and wherein the first face comprises a surface area that is larger relative to a surface area of the second face.

2. The threshing bar of claim 1, wherein the surface area of the first face is about 130% larger or about 1.3 times larger relative to the surface area of the second face.

3. The threshing bar of claim 1, wherein the surface area of the first face is about 170% larger or about 1.7 times larger relative to the surface area of the second face.

4. The threshing bar of claim 1, wherein the surface area of the first face is about 101% to 199% larger or about 1.01 times up to 1.99 times larger relative to the surface area of the second face.

5. A concave threshing bar, comprising:
    a concave having a pair of arcuate side members;
    a cylindrical threshing bar comprising a notch extending a length of the threshing bar, wherein the threshing bar is secured between the pair of arcuate side members of the concave; and
    the notch of the threshing bar comprising a first face and a second face, wherein the first face is sloped relative to the second face, and wherein the first or second face each comprise a surface area that is larger relative to each other.

6. The concave threshing bars of claim 5, wherein the first and second face are of varying dihedral angles.

7. The threshing bar of claim 5, wherein the surface area of the first face is about 130% larger or about 1.3 times larger relative to the surface area of the second face.

8. The threshing bar of claim 5, wherein the surface area of the first face is about 170% larger or about 1.7 times larger relative to the surface area of the second face.

9. The threshing bar of claim 5, wherein the surface area of the first face is about 101% to 199% larger or about 1.01 times up to 1.99 times larger relative to the surface area of the second face.

10. A concave threshing bar, comprising:
    a cylindrical threshing bar comprising a cut-out extending a length of the threshing bar, wherein the threshing bar is secured to a concave; and
    the cut-out of the threshing bar comprising a first surface and a second surface, wherein the first surface is at a sloped angle relative to the second surface, and wherein a surface area of the first face is at least about 101% to 199% larger or about 1.01 times up to 1.99 times larger relative to a surface area of the second face.

11. The concave threshing bars of claim 10, wherein the first and the second face are of varying dihedral angles.

12. The threshing bar of claim 10, wherein the surface area of the first face is further about 130% larger or about 1.3 times larger relative to the surface area of the second face.

13. The threshing bar of claim 10, wherein the surface area of the first face is further about 170% larger or about 1.7 times larger relative to the surface area of the second face.

* * * * *